United States Patent [19]

Kimble et al.

[11] Patent Number: 4,554,108

[45] Date of Patent: Nov. 19, 1985

[54] ALKALI CARBOXYALKYL DITHIOCARBAMATES AND USE AS ORE FLOTATION REAGENTS

[75] Inventors: Kenneth B. Kimble; Harold W. Mark; Clarence R. Bresson, all of Bartlesville, Okla.

[73] Assignee: Phillips Petroleum Company, Bartlesville, Okla.

[21] Appl. No.: 517,297

[22] Filed: Jul. 26, 1983

[51] Int. Cl.$^4$ .......................................... C07C 155/08

[52] U.S. Cl. .......................................... 260/455 A; 75/2

[58] Field of Search .......................................... 260/455 A

[56] References Cited

U.S. PATENT DOCUMENTS

| | | | |
|---|---|---|---|
| 3,329,266 | 7/1967 | Cox | 209/167 |
| 3,425,550 | 2/1969 | Baarson et al. | 209/166 |
| 3,464,551 | 9/1969 | Falvey | 209/166 |
| 3,940,488 | 2/1976 | Frohberger et al. | 260/455 A |

*Primary Examiner*—Henry R. Jiles
*Assistant Examiner*—Robert C. Whittenbaugh
*Attorney, Agent, or Firm*—French and Doescher

[57] ABSTRACT

Carboxyalkyl dithiocarbamates which can be characterized by the formula

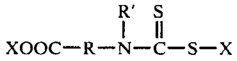

wherein R is selected from the group consisting of alkylene radicals, preferably alkylene radicals each having from 1 to 4 carbon atoms, wherein R' is selected from the group consisting of hydrogen and methyl and ethyl radicals, and wherein X is selected from the group consisting of alkali metal atoms, their use as ore flotation suppressants, and a process for making these novel compositions are disclosed.

8 Claims, No Drawings

ALKALI CARBOXYALKYL DITHIOCARBAMATES AND USE AS ORE FLOTATION REAGENTS

This invention relates generally to novel chemical compositions. In one aspect, the invention relates to a process for making such compositions. In another aspect, the invention relates to ore flotation processes employing such novel compositions.

Froth flotation is a process for recovering and concentrating minerals from ores. In a froth flotation process, the ore is crushed and wet ground to obtain a pulp. Additives such as mineral flotation or collecting agents, frothing agents, suppressants or depressants, stabilizers, etc., are added to the pulp to assist separating valuable minerals from the undesired or gangue portions of the ore in subsequent flotation steps. The pulp is then aerated to produce a froth at the surface. The minerals which adhere to the bubbles or froth are skimmed or otherwise removed and separated. The froth product or the reject product or both can then be further processed to obtain the desired minerals. Typical mineral flotation collectors include xanthates, amines, alkyl sulfates, arenes, sulfonates, dithiocarbamates, dithiophosphates, and thiols.

It is known from the art that some dithiocarbamates are useful as collecting agents. U.S. Pat. No. 3,464,551, for instance, describes dialkyl dithiocarbamates and the production thereof. U.S. Pat. No. 3,425,550 describes dialkyl dithiocarbamates and their production as well as the utility of these compounds as flotation collectors.

It is a continuing goal in the ore-processing industry to increase the productivity of ore flotation processes and, above all, to provide specific procedures which are selective to one ore or metal over other ores or metals present in the treated material.

It is an object of this invention to provide new dithiocarbamates.

A further object of this invention is to provide a process for making such dithiocarbamates.

Yet another object of this invention is to provide an ore flotation process wherein such new dithiocarbamates are used as flotation agents.

These and other objects, advantages, details, features and embodiments of this invention will become apparent to those skilled in the art from the following detailed description of the invention and the appended claims.

In accordance with this invention it has now been found that carboxyalkyl dithiocarbamate salts are very effective as suppressants in ore flotation processes.

Thus, in accordance with a first embodiment of this invention, novel compositions of matter are provided which can be characterized by the formula $$XOOC-R-\overset{R'}{\overset{|}{N}}-\overset{S}{\overset{\|}{C}}-S-X, \qquad (I)$$

wherein R is selected from the group consisting of alkylene radicals, preferably alkylene radicals each having from 1 to 4 carbon atoms; wherein R' is selected from the group consisting of hydrogen and methyl and ethyl radicals; and wherein X is selected from the group consisting of alkali metal atoms.

In accordance with a second embodiment of the invention there is provided a process for producing the above-defined novel dithiocarbamates. This process comprises reacting an aqueous alkali metal hydroxide, wherein the alkali metal is selected from the group consisting of Li, Na, and K, with an amino acid, preferably an amino acid characterized by the formula $$HOOC-R-\overset{R'}{\overset{|}{N}}-H, \qquad (II)$$

wherein R is selected from the group consisting of alkylene radicals, preferably alkylene radicals each having from 1 to 4 carbon atoms, and wherein R' is selected from the group consisting of hydrogen and methyl and ethyl radicals, and $CS_2$ to form a dithiocarbamate having the formula (I); and recovering the product of formula (I) as the product of the process.

The amino acids useful to produce the novel dithiocarbamates of the present invention include, for example, but are not limited to such materials as glycine, α-alanine, β-alanine, α-aminoisovaleric acid, and the like.

The detailed operating conditions for the individual steps are not critical and specific values for the steps can be seen from the following examples.

The separation of the product of formula (I) is carried out by standard techniques.

A further embodiment of this invention resides in an ore flotation process. More specifically, such further embodiment of this invention resides in a process for separating valuable ore materials from gangue materials. The ore flotation process of this invention distinguishes over the known ore flotation processes primarily in the employment of a new flotation agent to be defined. Otherwise the recovery process involves crushing of the ore and ore grinding to obtain a pulp. In this pulp the flotation agent is incorporated and the pulp is aerated to produce a froth at the surface which is rich in valuable ore materials but depleted of the gangue materials or vice versa. The ore materials, optionally, after additional flotation and frothing steps, are recovered. Frothing agents, selective suppressants and stabilizers which are well known in the art can be used in the various steps.

The dithiocarbamates useful in the ore flotation process of this invention are characterized by the formula $$XOOC-R-\overset{R'}{\overset{|}{N}}-\overset{S}{\overset{\|}{C}}-S-X, \qquad (I)$$

wherein R is selected from the group consisting of alkylene radicals, preferably alkylene radicals each having from 1 to 4 carbon atoms, R' is selected from the group consisting of hydrogen and methyl and ethyl radicals, and X is selected from the group consisting of alkali metal atoms. Examples of such compounds useful as suppressants or depressants in the process of this invention are those generally characterized as carboxyalkyl dithiocarbamates, such as for example:

disodium N-carboxymethyl dithiocarbamate,
disodium N-1-carboxyethyl dithiocarbamate,
disodium N-1-carboxypropyl dithiocarbamate,
disodium N-1-carboxybutyl dithiocarbamate, disodium (N-carboxymethyl-N-methyl) dithiocarbamate,
disodium (N-1-carboxyethyl-N-methyl) dithiocarbamate, disodium (N-1-carboxypropyl-N-methyl) dithiocarbamate,
disodium (N-1-carboxybutyl-N-methyl) dithiocarbamate, disodium (N-carboxymethyl-N-ethyl) dithiocarbamate,
disodium (N-1-carboxyethyl-N-ethyl) dithiocarbamate,
disodium (N-1-carboxypropyl-N-ethyl) dithiocarbamate,
disodium (N-1-carboxybutyl-N-ethyl) dithiocarbamate, dipotassium N-carboxymethyl dithiocarbamate,
dipotassium N-1-carboxyethyl dithiocarbamate,
dipotassium N-1-carboxybutyl dithiocarbamate, dilithium N-carboxymethyl dithiocarbamate,
dilithium N-1-carboxyethyl dithiocarbamate,
dilithium N-1-carboxypropyl dithiocarbamate, and the like, and combinations of any two or more thereof.

Hereinafter the designation N in the nomenclature of various carboxyalkyl dithiocarbamates will be omitted for convenience, but it will be understood that the dithiocarbamates so disclosed are those having the N-substitution.

The presently preferred compositions used as the ore flotation depressants in the process of this invention are disodium carboxymethyl dithiocarbamate and disodium 1-carboxyethyl dithiocarbamate.

The amount of carboxyalkyl dithiocarbamate employed in the process of this invention is not critical. The quantity will depend upon whether it is being used with an ore or a concentrate and whether there is a large or small amount of mineral to be suppressed. Generally, the amount of carboxyalkyl dithiocarbamate employed in the process will be in the range of from about 0.1 lb to about 10 lb of the inventive suppressant per ton of solids (lb/ton). Preferably the inventive ore flotation suppressant will be used in a quantity in the range from about 0.15 to about 5 lb/ton of solids.

It is generally believed that the carboxyalkyl dithiocarbamates disclosed herein are useful for suppressing or depressing the flotation of certain metal sulfide minerals during ore flotation processes. It is also understood that the carboxyalkyl dithiocarbamates may suppress a mixture of metals or minerals that are contained in a particular mining deposit or ore, said mixture being further separated by subsequent froth flotations or any other conventional separating methods. The carboxyalkyl dithiocarbamates herein disclosed are particularly useful for suppressing minerals based on copper, nickel, iron, lead and zinc from the total ore. Examples of such minerals include, but are not limited to such materials as

| | |
|---|---|
| Copper-bearing ores: | |
| Covellite | $CuS$ |
| Chalcocite | $Cu_2S$ |
| Chalcopyrite | $CuFeS_2$ |
| Bornite | $Cu_5FeS_4$ |
| Cubanite | $Cu_2SFe_4S_5$ |
| Valerite | $Cu_2Fe_4S_7$ or $Cu_3Fe_4S_7$ |
| Enargite | $Cu_3(As,Sb)S_4$ |
| Tetrahedrite | $Cu_{12}Sb_4S_{13}$ |

-continued

| | |
|---|---|
| Tennanite | $Cu_{12}As_4S_{13}$ |
| Cuprite | $Cu_2O$ |
| Tenorite | $CuO$ |
| Malachite | $Cu_2(OH)_2CO_3$ |
| Azurite | $Cu_3(OH)_2CO_3$ |
| Antlerite | $Cu_3SO_4(OH)_4$ |
| Brochantite | $C_4(OH)_6SO_4$ |
| Atacamite | $Cu_2Cl(OH)_3$ |
| Chrysocolla | $CuSiO_3$ |
| Famatinite | $Cu_3(Sb,As)S_4$ |
| Bournonite | $PbCuSbS_3$ |
| Lead-Bearing ore: | |
| Galena | $PbS$ |
| Zinc-Bearing ores: | |
| Sphalerite | $ZnS$ |
| Zincite | $ZnO$ |
| Smithsonite | $ZnCO_3$ |
| Chromium-Bearing ores: | |
| Daubreelite | $FeSCrS_3$ |
| Chromite | $FeO.Cr_2O_3$ |
| Iron-Bearing ores: | |
| Pyrite | $FeS_2$ |
| Marcasite | $FeS_2$ |
| Pyrrhotite | $Fe_7S_8$ |
| Nickel-Bearing ores: | |
| Pentlandite | $(FeNi)S$ |
| Millerite | $NiS$ |
| Niccolite | $NiAs$ |

The presently preferred ores in connection with which the process of this invention is applied are copper, zinc, lead and iron ores or minerals.

SEPARATION CONDITIONS

Any froth flotation apparatus can be used in this invention. The most commonly used commercial flotation machines are the Agitar (Galigher Co.), Denver Sub-A (Denver Equipment Co.), and the Fagergren (Western Machinery Co.). Smaller laboratory scale apparatus such as the Hallimond cell can also be used.

The instant invention was demonstrated in tests conducted at ambient room temperature to about 37° C. (100° F.) and atmospheric pressure. However, any temperature or pressure generally employed by those skilled in the art is within the scope of this invention.

The following examples serve to illustrate this invention without undue limitation of the scope thereof.

EXAMPLE I

This example describes the preparation of disodium carboxymethyl dithiocarbamate useful as a suspressant in ore flotation processes. To a 1-Liter round bottom flask fitted with a stirrer, thermometer, reflux condenser and a dropping funnel was added 253 milliliters of water and 84.0 grams (2.1 moles) of sodium hydroxide. After the NaOH had completely dissolved and the temperature had cooled below about 30° C., 75.0 grams (1.0 mole) of glycine was added and the mixture stirred until it was dissolved. Over the next 6 hours 76.14 grams (1.0 mole) of $CS_2$ was slowly added while the temperature was maintained below about 40° C. The reaction product mixture was considered to be a 40 percent aqueous solution of disodium carboxymethyl dithiocarbamate and was used as prepared in the subsequent ore flotation processes. Similarly, disodium 1-carboxyethyl dithiocarbamate was prepared from $\alpha$-alanine, $CS_2$ and NaOH.

EXAMPLE II

This example describes the evaluation of the dithiocarbamate prepared in Example I as a mineral suppressant using a mineral concentrate. To a 1.6 Liter Denver flotation cell was added 500 grams of a Cu/Pb/Fe-containing concentrate (Kidd Creek Concentrate) along with enough warm (30°-50° C.) water to raise the level of the float surface to within 1 to 2 inches from the top lip of the cell. The flotation reagent, collector or suppressant, to be used was added to the cell and the mixture conditioned at 900 rpm for 1 minute and then floated for 3 minutes. The new concentrate was then filtered, dried and analyzed. These results are listed in Table I where it can be seen that the inventive dithiocarbamate significantly suppresses the flotation of Cu, Pb and Fe (Runs 5 and 6) compared to when other chemically similar flotation reagents are used, glycine (Runs 3 and 4) and disodium carboxymethyl trithiocarbonate. In addition, the data shows the suppression is very effective over the concentration range of 0.16 lb/ton (Run 5) to 2.56 lb/ton (Run 6).

TABLE I

Effect of Carboxyalkyl Dithiocarbamate Salts as Ore Flotation Suppressants (500 grams Kidd Creek Concentrate)

| Run No. | Reagent | lb/ton | Wt. % Recovery (1 Test) Cu | Pb | Fe |
|---|---|---|---|---|---|
| 1 | None | — | 48.00 | 82.46 | 58.71 |
| 2 | Disodium Carboxymethyl Trithiocarbonate[a] | 0.4 | 37.30 | 77.41 | 52.15 |
| 3 | Glycine[b] | 0.16 | 51.30 | 88.05 | 64.76 |
| 4 | Glycine[b] | 2.56 | 48.65 | 90.05 | 61.65 |
| Invention: | | | | | |
| 5 | Disodium Carboxymethyl Dithiocarbamate[c] | 0.16 | 15.22 | 31.97 | 36.35 |
| 6 | Disodium Carboxymethyl Dithiocarbamate[c] | 2.56 | 14.04 | 34.36 | 36.16 |

[a]40 Wt. % Aqueous solution.
[b]2 Wt. % Aqueous solution of aminoacetic acid.
[c]40 Wt. % Aqueous solution of the reaction product from glycine, $CS_2$, NaOH.

EXAMPLE III

This example evaluates the inventive dithiocarbamate aqueous solution as a mineral suppressant using an ore body. About 740 grams of a Cu/Ni/Fe-containing ore (Falconbridge ore) along wth 350 milliliters of water and 0.19 grams (0.5 lb/ton) of CaO were ground in a ball mill for about 3 minutes. The ground mixture was transferred to a Denver flotation cell along with enough water to provide about a 30 weight percent aqueous slurry. Also added was 0.16 lb/ton sodium isopropyl xanthate as the collector. The mixture was conditioned for 2 minutes and floated for 7 minutes. The concentrate was filtered, dried and analyzed. The procedure was repeated and an average weight percent recovery estimated. In this manner there was obtained average weight percent recoveries of 81.13 percent Cu, 47.46 percent Ni, and 26.69 percent Fe. The procedure was repeated except that in addition to the xanthate collector selected reagents were also added to test their effectiveness as a suppressant. These results are listed in Table II where it can be seen that the glycine dithiocarbamate (Run 10) greatly suppresses the flotation of Cu, Ni and Fe when compared to the control where only the xanthate collector is used (Run 7). The results indicate that glycine by itself (Run 8) is relatively ineffective compared to the glycine dithiocarbamate derivative (Run 10). The results also indicate that a dithiocarbamate derivative of a glycine higher homolog, alanine (2-aminopropionic acid) is not quite as good a suppressant as the glycine derivative but it is still an effective suppressant (Run 11). For additional comparison a similar chemically structured suppressant was employed without the co- use of the xanthate collector. This material, a 40 weight percent aqueous solution of disodium carboxymethyl trithiocarbonate exhibited excellent Cu, Ni, and Fe suppression (Run 9).

TABLE II

Effect of Carboxyalkyl Dithiocarbamate Salts as Ore Flotation Suppressants (740 grams Falconbridge Ore)

| Run No. | | lb/ton | Average Wt. % Recovery (2 Runs) Cu | Ni | Fe |
|---|---|---|---|---|---|
| Control: | | | | | |
| 7 | Sodium isopropyl xanthate | 0.16 | 81.13 | 47.46 | 26.69 |
| 8 | Sodium isopropyl xanthate plus glycine[a] | 0.16<br>2.00 | 76.52 | 46.46 | 24.65 |
| 9 | Disodium Carboxymethyl Trithiocarbonate[b] | 5.00 | 5.64 | 4.75 | 4.52 |
| Invention | | | | | |
| 10 | Sodium isopropyl xanthate plus disodium carboxymethyl dithiocarbamate[c] | 0.16<br>5.00 | 7.54 | 6.66 | 4.98 |
| 11 | Sodium isopropyl xanthate plus disodium 1-carboxyethyl dithiocarbamate[d] | 0.16<br>5.00 | 11.68 | 11.82 | 5.56 |

[a]2 Wt. % aq. aminoacetic acid, $HOOCCH_2NH_2$.
[b]40 Wt. % aq. solution from Phillips Petroleum, $NaOOCCH_2SC(S)SNa$.
[c]40 Wt. % aq. solution. Reaction product of glycine, $CS_2$, NaOH.
[d]40 Wt. % aq. solution. Reaction product of α-alanine, $CS^2$, NaOH.

In summary, the data herein disclosed reveal that the novel carboxyalkyl dithiocarbamates of the present invention are useful as suppressants in ore flotation processes. The novel compounds are shown to be particularly suited for suppressing Cu, Fe, Pb and Ni.

Reasonable variations and modifications which will become apparent to those skilled in the art can be made in this invention without departing from the spirit and scope thereof.

We claim:

1. The composition represented by the formula

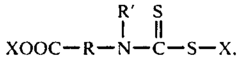

(I)

having from 3 to 8 carbon atoms; wherein R is selected from the group consisting of alkylene radicals; wherein R' is selected from the group consisting of hydrogen and methyl and ethyl radicals; and wherein X is selected from the group consisting of alkali metal atoms.

2. A composition in accordance with claim 1 wherein R is selected from the group consisting of alkylene radicals each having from 1 to 4 carbon atoms.

3. A composition in accordance with claim 2 wherein X is a sodium atom.

4. A composition in accordance with claim 1 wherein X is a sodium atom.

5. Carboxyalkyl dithiocarbamate selected from the group consisting of:

disodium N-carboxymethyl dithiocarbamate,
disodium N-1-carboxyethyl dithiocarbamate, disodium N-1-carboxypropyl dithiocarbamate,
disodium N-1-carboxybutyl dithiocarbamate, disodium (N-carboxymethyl-N-methyl) dithiocarbamate,
disodium (N-1-carboxyethyl-N-methyl) dithiocarbamate,
disodium (N-1-carboxypropyl-N-methyl) dithiocarbamate,
disodium (N-1-carboxybutyl-N-methyl) dithiocarbamate, disodium (N-carboxymethyl-N-ethyl) dithiocarbamate,
disodium (N-1-carboxyethyl-N-ethyl) dithiocarbamate,
disodium (N-1-carboxypropyl-N-ethyl) dithiocarbamate,
disodium (N-1-carboxybutyl-N-ethyl) dithiocarbamate, dipotassium N-carboxymethyl dithiocarbamate,
dipotassium N-1-carboxyethyl dithiocarbamate,
dipotassium N-1-carboxybutyl dithiocarbamate, dilithium N-carboxymethyl dithiocarbamate,
dilithium N-1-carboxyethyl dithiocarbamate,
dilithium N-1-carboxypropyl dithiocarbamate, and combinations of any two or more thereof.

6. Disodium carboxyalkyl dithiocarbamate selected from the group consisting of:

disodium N-carboxymethyl dithiocarbamate,
disodium N-1-carboxyethyl dithiocarbamate,
disodium N-1-carboxypropyl dithiocarbamate,
disodium N-1-carboxybutyl dithiocarbamate, disodium (N-carboxymethyl-N-methyl) dithiocarbamate,
disodium (n-1-carboxyethyl-N-methyl) dithiocarbamate,
disodium (N-1-carboxypropyl-N-methyl) dithiocarbamate,
disodium (N-1-carboxybutyl-N-methyl) dithiocarbamate, disodium (N-carboxymethyl-N-ethyl) dithiocarbamate,
disodium (N-1-carboxyethyl-N-ethyl) dithiocarbamate,
disodium (N-1-carboxypropyl-N-ethyl) dithiocarbamate,
disodium (N-1-carboxybutyl-N-ethyl) dithiocarbamate, and combinations of any two or more thereof.

7. Disodium carboxymethyl dithiocarbamate.

8. Disodium carboxyethyl dithiocarbamate.

* * * * *